(12) United States Patent
Fukusawa et al.

(10) Patent No.: US 8,194,967 B2
(45) Date of Patent: Jun. 5, 2012

(54) ARTICLE VISUAL INSPECTION APPARATUS

(75) Inventors: Mitsuyasu Fukusawa, Nyuzen-machi (JP); Hisayuki Kato, Kurobe (JP); Toshitaka Wakabayashi, Toyama (JP); Noboru Maekawa, Kurobe (JP)

(73) Assignees: YKK Corporation (JP); YKK AP Inc. (JP)

( * ) Notice: Subject to any disclaimer, the term of this patent is extended or adjusted under 35 U.S.C. 154(b) by 1021 days.

(21) Appl. No.: 11/883,152

(22) PCT Filed: Jan. 17, 2006

(86) PCT No.: PCT/JP2006/300923
§ 371 (c)(1),
(2), (4) Date: Jun. 19, 2008

(87) PCT Pub. No.: WO2006/080263
PCT Pub. Date: Aug. 3, 2006

(65) Prior Publication Data
US 2008/0310700 A1 Dec. 18, 2008

(30) Foreign Application Priority Data

Jan. 28, 2005 (JP) ................................ 2005-020535

(51) Int. Cl.
*G06K 9/00* (2006.01)
(52) U.S. Cl. ........................................................ 382/141
(58) Field of Classification Search .......... 382/141–152, 382/209, 218, 220, 302–304; 356/237.1–237.6
See application file for complete search history.

(56) References Cited

U.S. PATENT DOCUMENTS 7,388,979 B2 * 6/2008 Sakai et al. .................... 382/149
7,792,352 B2 * 9/2010 Sakai et al. .................... 382/149
7,865,011 B2 * 1/2011 Akimoto ........................ 382/149
2004/0165181 A1 8/2004 Kume et al.

FOREIGN PATENT DOCUMENTS

JP 61-245045 A 10/1986
JP 6-16855 U 4/1994

(Continued)

OTHER PUBLICATIONS

Office Action dated May 6, 2009 of corresponding Chinese Patent Application No. 200680002899.4.

(Continued)

*Primary Examiner* — Ishrat I Sherali
(74) *Attorney, Agent, or Firm* — Alston & Bird LLP

(57) ABSTRACT

An article visual inspection apparatus capable of detecting that the surface conditions of an article are so inferior as to render the article unusable as a product and rejecting the same as a defective article by inspecting the article for external defects, occurring on the surface of the article, such as streaks, dice marks and rough surfaces of an aluminum extruded shape. The visual inspection apparatus comprises an imaging device (1) for imaging the surface of the article, and an image processing device (3) for capturing the picked up image. The image processing device (3) has a plurality of image processing units that compare a captured image with a set judging reference value to evaluate the result, whereby the quality of surface conditions is evaluated based on external defects such as streaks, dice marks and rough surfaces of an aluminum extruded shape, and evaluations by the respective image processing units are weighted by a weighting unit to thereby comprehensively judge whether to accept or reject the article.

5 Claims, 3 Drawing Sheets

FOREIGN PATENT DOCUMENTS

| | | |
|---|---|---|
| JP | 06-229941 A | 8/1994 |
| JP | 08-086760 A | 4/1996 |
| JP | 08-145907 A | 6/1996 |
| JP | 08-145908 A | 6/1996 |
| JP | 2001-281155 A | 10/2001 |
| JP | 2004-061311 A | 2/2004 |

OTHER PUBLICATIONS

International Preliminary Report on Patentability of corresponding PCT/JP2006/300923 dated Jul. 31, 2007.

* cited by examiner (a)

(b)

(c)

ARTICLE VISUAL INSPECTION APPARATUS

TECHNICAL FIELD

The present invention relates to an article visual inspection apparatus for inspecting external defects occurring on the surface of an article, especially an aluminum extruded profile or shape extrusion-molded by an extruding machine.

BACKGROUND ART

Aluminum extruded shapes are articles that are extrusion-molded from a material such as aluminum or aluminum alloy by an extruding machine and are widely used, for example, in doors and windows.

The aluminum extruded shapes may have external defects occurring on the surfaces thereof. Depending on the degree of an external defect, the aluminum extruded shape cannot be used as a product due to its inferior surface condition. This give rise to a need for an inspection performed to determine as to whether an aluminum extruded shape has on its surface such an external defect as to render the aluminum extruded shape unusable and reject the aluminum extruded shape with such external defect as a defective article.

Conventionally, through visual inspection by a human operator, surface conditions of an aluminum extruded shape are checked for external defects that may occur on a surface of the aluminum extruded shape. If the inspected surface conditions of the aluminum extruded shape are determined to be unusable as a product due to external defects, the inspected aluminum extruded shape is rejected as a defective article.

However, the visual inspection by the human operator is insufficient in terms of reliability due to variations in skills in judging defective articles such that the judgment given to reject a defective article to be unusable as a product varies with the level of skill of the human operator and the inspection results depend on individual human operators.

With the difficulties in view, a visual inspection apparatus computerized to perform a visual inspection of aluminum extruded shapes is disclosed, for example, in Japanese Patent Laid-open Publication (JP-A) No. 2004-061311.

The disclosed visual inspection apparatus for aluminum extruded shapes is configured to take an image of the surface of an aluminum extruded shape by a camera immediately after the aluminum extruded shape is extrusion-molded from an extruding machine, detect the degree of a surface defect through image processing of the picked up image, and make a judgment about whether the inspected aluminum shape is to be an defective article depending on the degree of the surface defect.

Specifically, an image picked up from the surface of an aluminum extruded shape is divided into small areas each having predetermined widths in a main scanning direction perpendicular or normal to an extruding direction and an auxiliary scanning direction parallel to the extruding direction, respectively. At least two of the small areas are compared for their average shades, and an absolute value of the difference between maximum and minimum average shades is stored. Then the absolute value of the shade difference is compared with a reference value and if it is not less than the reference value, a judgment to reject a defective article is rendered.

The above-described conventional visual inspection apparatus is particularly effective for the inspection of so-called "streaks", that is, band-like patterns with different color tones along the extruding direction.

However, the external defects occurring on the surfaces of aluminum extruded shapes may include other external defects than the streaks.

For example, such external defects as so-called "dice marks" are "rough surfaces" may occur too.

The quality of surface conditions influenced by external defects such as dice marks, rough surfaces, and streaks can be detected through the afore-mentioned visual inspection performed by human operators. However, in the conventional external inspection apparatus, the quality of surface conditions involving a surface defect in the form of a dice mark, a rough surface cannot be occasionally detected.

Furthermore, the judgment of non-defective/defective articles based on the comparison of a shade difference obtained through image processing with a reference value, as done in the conventional visual inspection apparatus, cannot always secure reliable selection between non-defective articles and defective articles. For instance, judgments of non-defective/defective articles passed through the image processing may occasionally disagree with judgments of non-defective/defective articles made by human operators through visual inspection. Thus, it may occur that the articles, which were judged to be non-defective by the visual inspection apparatus, are judged to be defective at the visual inspection by the human operator, or alternatively, the articles that were judged to be defective by the visual inspection apparatus are judged to be non-defective at the visual inspection by the human operator.

It is accordingly an object of the present invention to provide a visual inspection apparatus, which can surely distinguish non-defective articles from defective articles, and is capable of detecting the quality of surface conditions based on external defects, such as streaks, dice marks and rough surfaces, occurring on the surface of an aluminum extruded shape to thereby ensure that an aluminum extruded shape having surface conditions so inferior as to render the aluminum extruded shape unusable as a product can be rejected as an defective article.

DISCLOSURE OF THE INVENTION

According to the present invention, there is provided an article visual inspection apparatus, which is capable of distinguishing non-defective articles and defective articles with certainty, and which comprises an imaging device 1 for imaging a surface of an article, and an image processing device 3 that captures an image picked up by the imaging device 1. The image processing device has a plurality of image processing units, and each of the image processing units compares a captured image with a judging reference value set for each image processing unit to evaluate the result. The image processing device 3 further includes a weighting unit, and the weighting unit performs a weighting of evaluations of the respective image processing units to thereby judge whether to accept or reject the article.

It is preferable according to the present invention that the plurality of image processing units is configured to perform the functions of detecting a brightness of the captured image within a set inspection area, and comparing the detected brightness with a judgment reference value to evaluate the result; dividing the inspection area of the captured image into a plurality of inspection blocks, detecting a brightness of the captured image in each of the inspection blocks, and comparing the detected brightness with a judging reference value to evaluate the result; and setting a small region within the inspection area of the captured image, moving the small region, detecting a brightness of the captured image in the small region while the small region is present at each of a plurality of preset position during movement, and comparing the detected brightness with a judging reference value to evaluate the result.

With this arrangement, since the brightness detection is performed at each of the set inspection area, the divided inspection blocks, and the small region moving across the inspection area and the detected brightness is compared with a judging reference value to evaluate the result, it is possible to detect external defects with certainty to thereby facilitate accurate judgment of the non-defective/defective article.

Preferably, the image processing device includes a first image processing unit, a second image processing unit, a third image processing unit, a fourth image processing unit and a fifth image processing unit. The first image processing unit compares a brightness difference between a light part and a dark part of the captured image with a first judging reference value to evaluate the result. The second image processing unit compares a brightness difference rate of the dark part to the light part with a second judging reference value to evaluate the result. The third image processing unit divides the captured image into a plurality of inspection blocks, calculate a brightness difference in each of the divided inspection blocks, and compares the number of inspection blocks having brightness differences greater than a brightness difference threshold value with a third judging reference value to evaluate the result. The fourth image processing unit divides the captured image into a plurality of inspection blocks, calculates a maximum average brightness difference on the basis of an average brightness in each of the divided inspection blocks, and compares the maximum average brightness difference with a fourth judging reference value to evaluate the result. The fifth image processing unit calculates a brightness kurtosis in each of plural small regions of the captured image, and compared a maximum brightness kurtosis of the calculated brightness kurtosis values with a fifth judging reference value to evaluate the result.

It is preferable according to the present invention that the weighting unit multiplies evaluations detected by the respective image processing units by weighting factors, respectively, adds up all the multiplied values, and compares the sum with a judging reference value to judge whether to accept or reject the article.

With this arrangement, when evaluations by the respective image processing units are to be weighted by the weighting unit, the evaluations are multiplied by weighting factors, respectively, then the thus multiplied evaluations are added to each other, and the sum is compared with a judging reference value to judge whether to accept or reject the article. By thus performing the weighting, it is possible to change the effects of the respective evaluations on the final judgment, making it possible to perform a reliable detection of external defects and an inspection comparable to a visual observation. In addition, it becomes possible to identify the type of external defect.

Preferably, the weight given to each of the evaluations is determined, for each image processing process to be evaluated, on the basis of the effect or influence of the evaluation on the external appearance of the article.

For example, such an evaluation, which can exert great influence on the article external appearance, is multiplied by a large weighting factor to thereby increase the importance of the evaluation. Alternatively, the evaluation with small degree of influence is multiplied by a small weighting factor to thereby lower the importance of the evaluation.

By thus determining the weighting factors, the sum of weighted values becomes substantially equal to a judgment value used in a visual inspection by a human operator, enabling the inspection to be carried out in the same manner as the visual inspection by the human operator.

The effect on the external appearance of the article may include the visibility of an external defect and the invisibility of an external defect subsequent to a post treatment of the article.

Preferably, the article to be imaged is an aluminum extruded shape 5 in which instance the imaging device 1 is disposed on an extrusion side of an extruding machine for imaging a surface of the aluminum extruded shape 5 immediately after extrusion thereof. The image processing device 3 further includes a preprocessing unit 7 for preprocessing the captured image. The preprocessing unit 7 has a function to correct an image blurring occurring due to vibrations of the aluminum extruded shape during extrusion to thereby form an image free of blurring.

With this arrangement, since the first to fifth image processing units are allowed to perform image-processing operations on the basis of the blurring-free image, it is possible to detect an defective article with reliability to reject the same.

According to the present invention, an illuminating device 2 may be provided for illuminating that part of the article to be imaged. Preferably, the illuminating device 2 includes two illuminating units 2a. Each of the illuminating units 2a is able to adjust the projecting direction of light independently from another illuminating unit.

This arrangement ensures that in view of a step formed on the surface of the aluminum extruded shape, light can be projected onto both a higher surface portion and a lower surface portion in an appropriate manner to thereby insure accurate inspection of the surface conditions of a stepped surface.

BEST MODE FOR CARRYING OUT THE INVENTION

Figure 1:
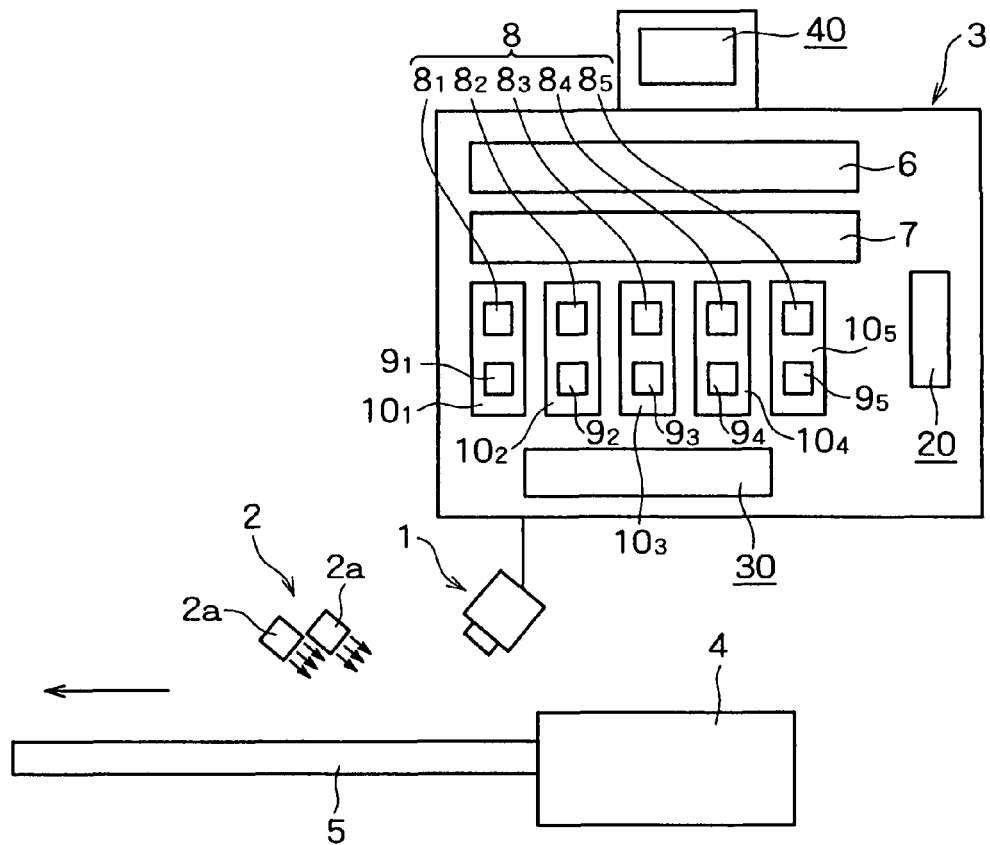
FIG. 1 is a diagrammatical view explanatory of the configuration of a visual inspection apparatus according to the present invention.
Figure 2:
FIG. 2 is a detailed explanatory view of an illuminating device.
Figure 2:
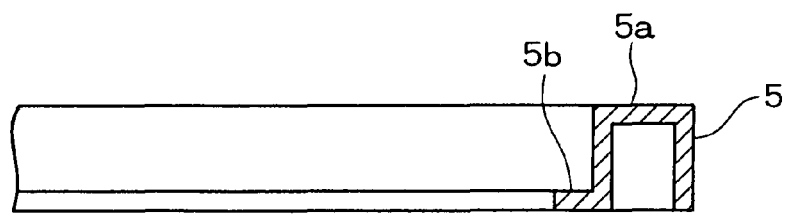

As shown in FIG. 1, a visual inspection apparatus according to the present invention generally comprises an imaging device 1, an illuminating device 2 and an image processing device 3.

At an extruding machine 4 an aluminum extruded profile or shape 5 is extruded in a direction of the arrow. The aluminum extruded shape 5 is an article to be inspected.

The imaging device 1 forms images of a surface of the aluminum extruded shape 5. An example of such imaging device 1 is a line sensor camera that picks up images on the surface of the aluminum extruded shape 5 in a direction perpendicular or normal to the extruding direction.

The illuminating device 2 illuminates the surface of the aluminum extruded shape. An example of the illuminating device 2 is a light emitting diode (LED) that emits coherent light onto a part of the surface of the aluminum extruded shape 5 where imaging by the imaging device is taken.

The image processing device 3 includes an image capturing section or unit 6 that captures an image of the surface of the aluminum extruded shape 5 which was taken or picked up by the imaging device 1, a preprocessing section or unit 7 that performs a preprocessing of the captured image, a plurality of image processing sections or units 10 that, on the basis of the preprocessed image, perform comparisons with sets of judging reference values as an image processing operation to evaluate the results, a weighting section or unit 20 that perform weightings of evaluations of the respective image processing units 10, a judging section or unit 30 that, on the basis of the weighted results, estimates the degree of an external defect (i.e., surface conditions) on the surface of the aluminum extruded shape 5 as an inspected article to thereby judge whether to accept or reject the article, and a monitor 40 that displays the judgment result.

The image processing units 10 each include an arithmetic part 8 that performs an arithmetic operation based on the captured image, and an evaluation part 9 that performs evaluation by comparing the result of arithmetic operation with a judging reference value.

In the illustrated embodiment, there are provided five image processing units, i.e., the first, second, third, fourth and fifth image processing units $10_1$, $10_2$, $10_3$, $10_4$, and $10_5$.

The imaging device 1 is located on an extrusion side of the extruding machine 4 to pick up an image of that part of the surface of the aluminum extruded shape which has just been extruded from the extruding machine 4. The picked up image is immediately transmitted to the image processing device 3.

With this arrangement, the aluminum extruded shape can be subjected to visual inspection immediately after extrusion thereof, and therefore, by stopping the extruding machine 4 upon rejection of a defective article by the image processing device 3, it is possible to reduce the occurrence of additional defective articles.

The position of the imaging device 1 should by no means be limited to the aforesaid position but may include a position on a conveyance line subsequent to an alumite treatment station of the aluminum extruded shape, in which instance an image of the alumite-treated surface is picked up for enabling a visual inspection. Alternatively, the imaging device 1 may be disposed on a conveyance line subsequent to a painting station for imaging the coated surface to perform a visual inspection of the aluminum extruded shape 5.

The imaging device 1 shown in FIG. 1 is arranged to image an upper surface of the aluminum extruded shape 5, however, the invention may include an arrangement where the imaging device 1 is disposed to image a lower surface or a side surface of the aluminum extruded shape 5.

Furthermore, the number of the imaging device 1 may be plural and the plural imaging devices 1 are arranged to image a plurality of surfaces of the aluminum extruded shape 5. In this instance, the judgment of non-objective/objective articles is performed on the basis of the image of each surface of the aluminum extruded shape 5.

The illuminating device 2 includes a plurality of illuminating units 2a such as LEDs. Each of the illuminating units 2a is able to adjust the light projecting direction so that according to surface conditions of the aluminum extruded shape 5, the light projecting direction can be adjusted to enable a stepped surface to be properly imaged by the imaging device 1.

For example, when the aluminum extruded shape 5 has a surface configuration including a step having a higher surface portion 5a and a lower surface portion 5b, one illuminating unit 2a is adjusted to illuminate the higher surface portion 5a, and another illuminating unit 2b is adjusted to illuminate the lower surface portion 5b so that both surface portions 5a and 5b can receive the same illumination.

In other words, if only one illuminating unit 2a is employed, the higher surface portion 5a while being illuminated by the illumination unit 2a will produce a shadow on the lower surface portion 5b, hindering reliable imaging of the lower surface portion 5b.

With the illuminating device 2 arranged as in the illustrated embodiment, it is possible for the imaging device 1 to image the stepped surface under uniform conditions, leading to an accurate inspection of surface conditions of the stepped surface.

As for the adjustment of the illuminating unit 2a, it may be achieved manually, but preferably it is set on the basis of information about the shape and configuration of an aluminum extruded shape to be inspected.

The illuminating device 2 may include other devices than as described above. For instance, it may utilize natural sunlight in which instance an optical fiber is used to collect sunlight and illuminate an inspection surface with sunlight. In this instance, the illuminating device makes use of sunlight via a control device, which controls the light intensity and direction of sunlight.

The illuminating device 2 may be omitted in which instance spatial light at an installation side of the visual inspection apparatus is used.

The image picked up by the imaging device 1 is captured at the image capturing unit 6. If the aluminum extruded shape 5 has on its surface an external defect, the external defect appears in the captured image as a belt-like part, which extends continuously in the extruding direction and has a different brightness from other parts arranged in a direction normal to the extruding direction.

This is because that part of the aluminum extruded shape surface, which includes an external defect, differs in brightness from the remaining part of the aluminum extruded shape surface, which is free of the external defect. Accordingly, the captured image has belt-like parts of different brightnesses according to the external defect involved in the aluminum extruded shape surface.

The preprocessing unit 7 edits the captured image so as to facilitate inspection. For example, if the captured image is blurry, the preprocessing unit 7 modifies the blurry image into an image free from blurring.

Since the aluminum extruded shape 5, as it is extruded continuously from the extruding machine 5, vibrates in a direction normal to the extruding direction, and since the imaging device 1 takes an image of the thus vibrating aluminum extruded shape 1, the belt-like parts on the captured image have a wavy shape in the extruding direction rather than a rectilinear shape. This phenomenon is called image blurring.

When the image blurring occurs, the preprocessing unit 7 performs image modification to rectify the wavy belt-like parts into a rectilinear shape in the extruding direction.

As an alternative, it is possible to mechanically vibrate the imaging device 1 in the vibrating direction of the aluminum extruded shape in synchronism with the vibration of the aluminum extruded shape to thereby enable an image to be captured without blurring.

The arithmetic parts 8 calculate various values based on the brightness differences in inspection areas of the captured image of the surface of the aluminum extruded shape 5. In the illustrated embodiment, there are provided five arithmetic parts, i.e., the first, second, third, fourth and fifth arithmetic parts $8_1$, $8_2$, $8_3$, $8_4$ and $8_5$.

The evaluation parts 9 perform evaluations by comparing the various values calculated by the arithmetic parts 8 with various judging reference values set for respective image processing units $10_1$, $10_2$, $10_3$, $10_4$, and $10_5$. In the illustrated embodiment, there are provided five evaluation parts, i.e., the first, second, third, fourth and fifth evaluation parts $9_1$, $9_2$, $9_3$, $9_4$ and $9_5$.

Next, an arithmetic operation performed by the first arithmetic part $8_1$ and an evaluation performed by the first evaluation part $9_1$ will be described below.

Figure 3:
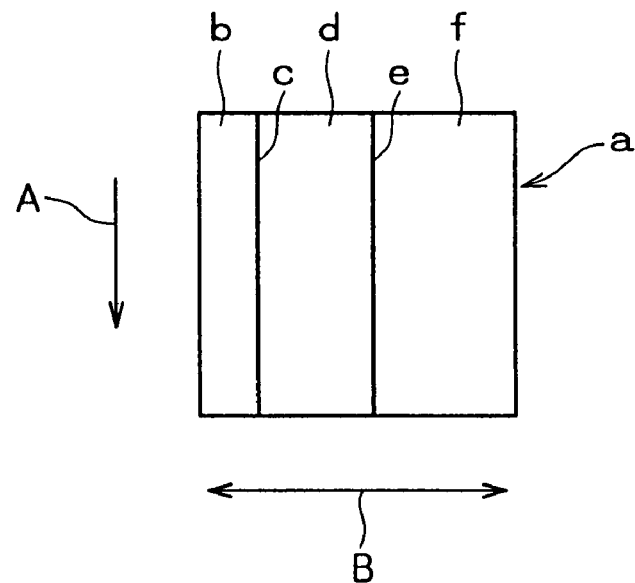
FIG. 3 is a diagrammatical view explanatory of a way of detecting the brightness of an image within an inspection area.

As shown in FIG. 3, an inspection area "a" of the captured image has five regions "b", "c", "d", "e" and "f" of different brightnesses arranged side by side in a direction B normal to the extruding direction A, with the regions "c" and "e" forming belts along the extruding direction A.

The first arithmetic part $8_1$ detects brightnesses of the respective regions "b", "c", "d", "e" and "f" and calculates a difference (maximum brightness difference) $X_1$ between the maximum brightness and the minimum brightness.

The first evaluation part $9_1$ has a first brightness difference judging reference value $C_1$ and a second brightness difference judging reference value $C_2$, which is greater than the first brightness difference judging reference value $C_1$.

When the maximum brightness difference $X_1$ is smaller than the first brightness difference judging reference value $C_1$, it is evaluated that the possibility of the non-defective article is high.

When the maximum brightness difference $X_1$ is greater than the first brightness difference judging reference value $C_1$ and smaller than the second brightness difference judging reference value $C_2$, it is evaluated as being an "intermediate article".

When the maximum brightness difference $X_1$ is greater than the second brightness difference judging reference value $C_2$, it is evaluated that the possibility of the defective article is high.

By the first arithmetic part $8_1$ and the first evaluation part $9_1$, it is determined whether the degree of external defects, such as undue streaks and rough surfaces, occurring on the surface of the aluminum extruded shape 5 are so inferior as to render the aluminum extruded shape unusable as a product.

Since the surface portion including the external defect, which is called "streak", differs in reflection of light from other surface portions, there are formed belts of different brightnesses on the captured image. As the brightness difference becomes greater, the external defect, which is called streak, becomes more remarkable.

Thus, the first arithmetic part $8_1$ and the first evaluation part $9_1$ jointly constitute a first image processing unit $10_1$, which compares the brightness difference between a bright portion and a dark portion of the captured image with judging reference values to evaluate the result.

Then, an arithmetic operation performed by the second arithmetic part $8_2$ and an evaluation performed by the second evaluation part $9_2$ will be described below.

The second arithmetic part $8_2$ detects a maximum brightness and a minimum brightness in the inspection area "a" shown in FIG. 3 in the same manner as the first arithmetic part $8_1$ and calculates a brightness difference rate $X_2$, which is the rate of the minimum brightness to the maximum brightness (minimum brightness/maximum brightness).

The second evaluation part $9_2$ has a first brightness difference rate judging reference value $D_1$ and a second brightness difference rate judging reference value $D_2$. The first brightness difference rate judging reference value $D_1$ is greater than the second brightness difference rate judging reference value $D_2$.

When the brightness difference rate $X_2$ is greater than the first brightness difference rate judging reference value $D_1$, it is evaluated that the possibility of the non-defective article is high.

When the brightness difference rate $X_2$ is smaller than the first brightness difference rate judging reference value $D_1$ and greater than the second brightness difference rate judging reference value $D_2$, it is evaluated as being an "intermediate article".

When the brightness difference rate $X_2$ is smaller than the second brightness difference rate judging reference value $D_2$, it is evaluated that the possibility of the defective article is high.

By the second arithmetic part $8_2$ and the second evaluation part $9_2$, it is possible to detect those external defects, such as undue streaks and rough surfaces, which could not be detected by the first arithmetic part $8_1$ and the first evaluation part $9_1$, and based on this detection, it is determined whether the surface conditions are so inferior as to render the aluminum extruded shape unusable as a product.

The visibility of the external defect, which is called streak, depends on the contrast between light and dark in the whole surface of the aluminum extruded shape such that it is more distinguishable for a darker surface than for a lighter surface. Accordingly, when the whole surface of an aluminum extruded shape is dark, the streak is highly visible and, hence, even if the afore-mentioned brightness difference is smaller than the first brightness difference judging reference value, it should be evaluated that the possibility of the defective article is high. However, for the first arithmetic part $8_1$ and the first evaluation part $9_1$, reliable detection of such streak is impossible to perform.

In view of this, the contrast of the whole surface of the aluminum extruded shape is taken into account by way of a brightness difference rate so that even if the afore-mentioned brightness difference is smaller than the first brightness difference judging reference value, when the brightness difference rate is small, it is evaluated that the possibility of the defective article is high.

Thus, the second arithmetic part $8_2$ and the second evaluation part $9_2$ jointly constitute a second image processing unit $10_2$, which compares the brightness difference rate between a dark portion and a bright portion (minimum brightness/maximum brightness) of the captured image with judging reference values to evaluate the result.

Next, description will be made to an arithmetic operation performed by the third arithmetic part $8_3$ and an evaluation performed by the third evaluation part $9_3$.

Figure 4:
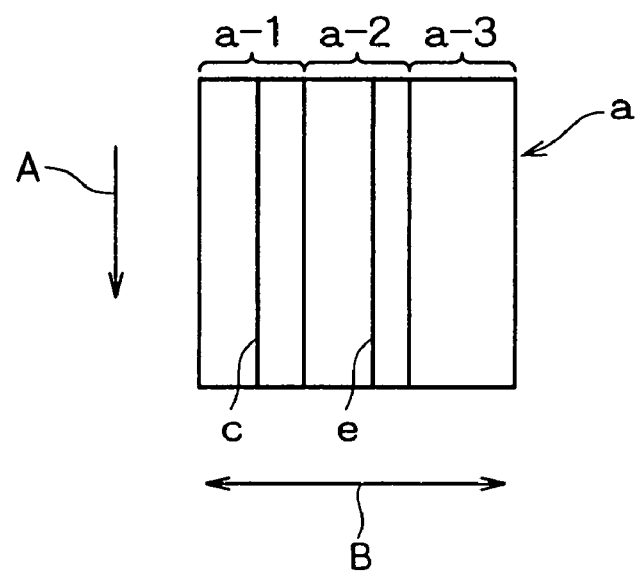
FIG. 4 is a diagrammatical view explanatory of another way of detecting the brightness of an image within an inspection area.

As shown in FIG. 4, the inspection area "a" is divided into plural inspection blocks in the direction B normal to the extrusion direction A. In the illustrated embodiment, first, second and third inspection blocks a-1, a-2 and a-3 are provided.

For each of the divided inspection blocks, brightness is detected to calculate a difference (maximum brightness difference) between the maximum brightness and the minimum brightness in the same manner as described above. The maximum bright difference is thus calculated for each of the first, second and third inspection blocks a-1, a-2 and a-3.

Each of the calculated brightness differences is compared with a brightness difference threshold value to determine the number of inspection blocks with maximum brightness differences exceeding the brightness difference threshold value, and the determined number of inspection blocks is divided by the total number of inspection blocks to thereby calculate an inspection block brightness difference $X_3$ (the number of inspection blocks with brightness differences exceeding the threshold value/the total number of inspection blocks). For instance, when the first and second inspection blocks a-1 and a-2 have maximum brightness differences greater than the brightness difference threshold, the inspection block brightness difference $X_3$ is 0.67 (=⅔).

The third evaluation part $9_3$ has a first inspection block brightness difference judging reference value $E_1$ and a second inspection block brightness difference judging reference value $E_2$, which is greater than the first inspection block brightness difference judging reference value $E_1$.

When inspection block brightness difference $X_3$ is smaller than the first inspection block brightness difference judging reference value $E_1$, it is evaluated that the possibility of the non-defective article is high.

When the inspection block brightness difference $X_3$ is greater than the first inspection block brightness difference judging reference value $E_1$ and smaller than the second inspection block brightness difference judging reference value $E_2$, it is evaluated as being an "intermediate article".

When the inspection block brightness difference $X_3$ is greater than the second inspection block brightness difference judging reference value $E_2$, it is evaluated that the possibility of the defective article is high.

By the third arithmetic part $8_3$ and the third evaluation part $9_3$, the external defect, which is so called "rough surface", is detected and when the detected external defect is so inferior as to render the aluminum extruded shape unusable as a product, it is rejected as a detective article.

When the external defect occurs in the form of fine irregular spots of narrow widths arrayed over the entire surface (the entire area in a direction normal to the extruding direction) of the aluminum extruded surface, it is called rough surfaces.

In this instance, the captured image may have a number of parts of different brightnesses arrayed with a narrow width in a direction normal to the extruding direction. Accordingly, if the captured image is divided into plural inspection blocks, the number of inspection blocks whose inspection block brightness differences are greater than the judging reference value is larger than the rest. Thus, by doing as described above, the external defect, which is called rough surface, can be detected.

Thus, the third arithmetic part $8_3$ and the third evaluation part $9_3$ jointly constitutes a third image processing unit $10_3$, which divides the captured image into plural inspection blocks, calculates a brightness difference in each of the inspection blocks, and compares the number of inspection blocks having brightness differences greater than the brightness difference threshold value with judging reference values to evaluate the result.

Then, description will be made to an arithmetic operation performed by the fourth arithmetic part $8_4$ and an evaluation performed by the fourth evaluation part $9_4$.

As shown in FIG. 4, the inspection area "a" is divided into plural inspection blocks. In the illustrated embodiment, first, second and third inspection blocks a-1, a-2 and a-3 are provided.

For each of the divided inspection blocks, brightnesses in a direction normal to the extruding direction are sequentially detected to thereby detect an average brightness.

The detected average brightnesses of the respective inspection blocks are compared with one another to calculate a difference (maximum average brightness difference) $X_4$ between the maximum average brightness and the minimum average brightness.

The fourth evaluation part $9_4$ has a first maximum average brightness difference judging reference value $F_1$ and a second maximum average brightness difference judging reference value $F_2$. The first maximum average brightness difference judging reference value $F_1$ is smaller than the second maximum average brightness difference judging reference value $F_2$ ($F_1 < F_2$).

When the maximum average brightness difference $X_4$ is smaller than the first maximum average brightness difference judging reference value $F_1$, it is evaluated that the possibility of the non-defective article is high.

When the maximum average brightness difference $X_4$ is greater than the first maximum average brightness difference judging reference value $F_1$ and smaller than the second maximum average brightness difference judging reference value $F_2$, it is evaluated as being an "intermediate article".

When the maximum average brightness difference $X_4$ is greater than the second maximum average brightness difference judging reference value $F_2$, it is evaluated that the possibility of the defective article is high.

By the fourth arithmetic part $8_4$ and the fourth evaluation part $9_4$, the external defect, which is called streak, can be detected.

Thus, the fourth arithmetic part $8_4$ and the fourth evaluation part $9_4$ jointly constitute a fourth image processing unit $10_4$, which divides the captured image into plural inspection blocks, calculates a maximum average brightness difference on the basis of average brightnesses of the respective inspection blocks, and compares the maximum average brightness difference with judging reference values to evaluate the result.

Next, description will be made to an arithmetic operation performed by the fifth arithmetic part $8_5$ and an evaluation performed by the fifth evaluation part $9_5$.

Figure 5:
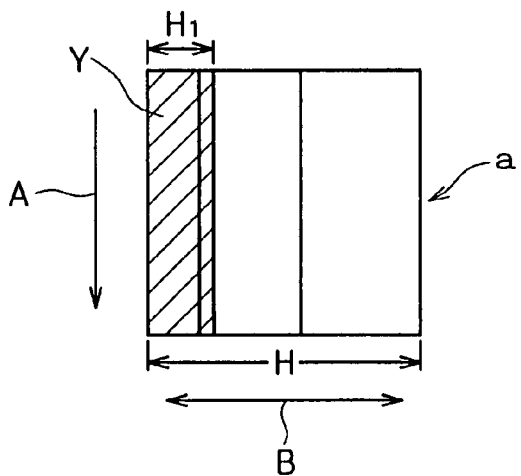
FIG. 5 is a diagrammatical view explanatory of still another way of detecting the brightness of an image within an inspection area.
Figure 5:
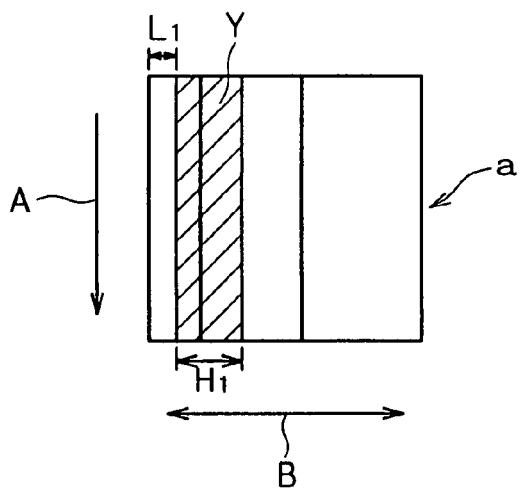
Figure 5:
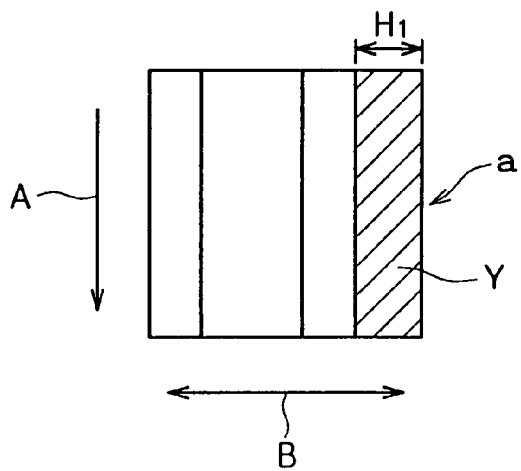

As shown in FIG. 5(*a*), a small region Y (indicated by hatching) having a width $H_1$ smaller than the entire width H (a size in a direction normal to the extruding direction) of the inspection area "a" of the captured image is set within the inspection area "a".

The small region Y is moved from one end in the width direction shown in FIG. 5(*a*) to the other end in the width direction in a sequential manner over a predetermined travel distance $L_1$, as shown in FIGS. 5(*b*) and 5(*c*), and for each small region Y which has moved the predetermined travel distance $L_1$, the brightness is detected in the same manner as described above. The travel distance $L_1$ is smaller than the width $H_1$ of the small region Y.

For each small region Y a maximum brightness within the small region and brightnesses at both widthwise ends of the small region Y are extracted, then a difference between the maximum brightness and the brightness at one widthwise end and a difference between the maximum brightness and the brightness at the other widthwise end are calculated, respectively, and the brightness differences are added to each other to thereby detect a brightness kurtosis in each small region Y.

Then, a maximum value in brightness kurtosis (maximum brightness kurtosis value) $X_5$ of the respective small regions Y is calculated. In this instance, the width direction means a direction of movement of the small region.

The fifth evaluation part $9_5$ has a first brightness kurtosis judging reference value $G_1$ and a second brightness kurtosis judging reference value $G_2$. The first brightness kurtosis judging reference value $G_1$ is smaller than the second brightness kurtosis judging reference value $G_2$ ($G_1 < G_2$).

When the maximum brightness kurtosis value $X_5$ is smaller than the first maximum brightness kurtosis judging reference value $G_1$, it is evaluated that the possibility of the non-defective article is high.

When the maximum brightness kurtosis value $X_5$ is greater than the first maximum brightness kurtosis judging reference value $G_1$ and smaller than the second brightness kurtosis judging reference value $G_2$, it is evaluated as being an intermediate article.

When the maximum brightness kurtosis value $X_5$ is greater than the second maximum brightness kurtosis judging reference value $G_2$, it is evaluated that the possibility of the defective article is high.

By the fifth arithmetic part $8_5$ and the fifth evaluation part $9_5$, the external defect, which is called dice mark, is detected and when the detected external defect is so inferior as to render the aluminum extruded shape unusable as a product, it is rejected as a detective article.

When the surface of the aluminum extruded shape has a belt-like part, which is especially lighter than the other part, the belt-like part is designated as an external defect called "dice mark".

In this instance, an especially light belt-like part is present on the captured image. Accordingly, if a maximum one of the brightness kurtosis values that have been calculated for plural small regions on the captured image (inspection area) is greater than a judging reference value, this means that a specially light belt-like part is present. Thus, the external defect, which is called dice mark, occurring on the surface of the aluminum extruded shape can be detected to reject the defective article.

Thus, the fifth arithmetic part $8_5$ and the fifth evaluation part $9_5$ jointly constitutes a fifth image processing unit $10_5$, which calculates a brightness kurtosis for each of plural small regions on the captured image, and compares a maximum brightness kurtosis with judging reference values to evaluate the result.

In order to judge the article to be non-defective, defective or intermediate on the basis of evaluations on the possibilities of non-defective, defective and intermediate articles given at the first, second, third, fourth and fifth image processing units $10_1$, $10_2$, $10_3$, $10_4$ and $10_5$ through comparisons with judgment reference values, the image processing device 3 is associated with the weighting unit 20 as shown in FIG. 1. The weighting unit 20 is provided to comprehensively judge the findings or detections at the five image processing units so that based on the weighted values, the judging unit 30 makes a final judgment as to whether the article is non-defective, defective or intermediate.

Next, the weighting unit 20 will be described later in greater detail.

The weighting unit 20 multiplies an evaluated value obtained at each of the image processing units $10_1$, $10_2$, $10_3$, $10_4$ and $10_5$ by a predetermined weighting factor to thereby represent an evaluation by way of a weighted value.

The evaluations represented by the respective weighted values are added up at the judging unit 30, and the added value or sum is compared with a judging reference value to thereby finally determine the product to be non-defective, defective or intermediate.

In this determination, if the evaluation, which is given when the possibility of the non-defective article is high, is represented by a big figure and the evaluation, which is given when the possibility of the defective article is high, is represented by a small figure, when the sum of the values multiplied by the weighting factors is greater than a judging reference value (a figure set as a reference), it is judged to be a non-defective article. On the other hand, when the former is less than the latter, it is judged to be a defective article.

For determination of an intermediate article, two judging reference values, one larger than the other, are provided. When the added value obtained as above is in between the two judging reference values, it is judged to be an intermediate article.

Alternatively, in this determination, if the evaluation, which is given when the possibility of the defective article is high, is represented by a big figure and the evaluation, which is given when the possibility of the non-defective article is high, is represented by a small figure, when the added value is greater than a judging reference value, it is judged to be a defective article. Alternatively, when the added value is smaller than the judging reference value, it is judged to be a non-defective value. For determination of an intermediate article, two judging reference values are provided in the same manner as described above.

For example, the evaluated values obtained at the first to fifth evaluation parts $9_5$ to $9_5$ are multiplied by predetermined weighting factors, respectively, to thereby weight the evaluations.

The weighting factors are determined based on the effect that evaluations by the first to fifth evaluation parts $9_5$ to $9_5$, produce on the external appearance of the article. Specially, the weighting factor increases as the effect becomes large and decreases as the effect becomes small. In other words, the factors used for weighting are so set as to realize the judgments or determinations obtained through visual inspection by a human inspector.

As an example, the factors are set such that an aluminum extruded shape which is judged to be defective through visual inspection by the human operator, is judged to be defective when subjected to actual judgment by the visual inspection apparatus.

With this weighting, it may occur that an article, which has been evaluated as probably defective at any of the image processing units, is finally judged as non-defective.

By thus performing the judgment using the weighted evaluations, it is possible to surely find out external defects, such as streaks, dice marks and rough surfaces. In addition, it becomes possible to identify the type of external defect, too. In a word, weighting is to set degrees of importance for the evaluations in order to render the judgement by the visual inspection apparatus comparable with the judgment obtained through visual inspection by a human inspector.

When an external defect is detected, a signal may be sent to a control unit to stop operation of the extruding machine 4 or to perform control of the extrusion speed automatically. With this arrangement, it is possible to reduce the amount of defective articles.

The aluminum extruded shape is subsequently subjected to a post-extrusion treatment, such as alumite treatment, painting or the like surface treatment. The judgment may be done in view of the type of surface treatment.

For instance, by virtue of the alumite treatment or the painting (surface treatment) effected on the aluminum extruded shape after extrusion, depending on the type of surface treatment, the inspection result obtained at the first image processing unit may give only an small effect on the possibility of becoming an external defect. In this instance, the weighting is achieved to lower the importance of the first evaluation. Alternatively, when the evaluation by the second image processing unit is absolutely important for that type of surface treatment, the importance of the second evaluation is increased.

By thus setting the weighting factors, it is possible to perform judgment in conformity with the type of surface treatment. Additional to the discrimination between non-defective articles and defective articles, the type of surface treatment can be taken into account in making a judgment with the result that the amount of disposal of defective articles caused due to external defects can be reduced.

In the foregoing description, the term "non-defective article" is used to refer to an aluminum extruded shape having an external appearance, which is so superior as to render the aluminum extruded shape usable as a product. On the other hand, the term "defective article" is used to refer to an aluminum extruded shape having an external defect, which is so inferior as to render the aluminum extruded shape unusable as a product. Similarly, the term "intermediate article" is used to refer to an aluminum extruded shape having an external defect to the extent that a mechanical inspection cannot determine whether to accept or reject the external defect.

As for the non-defective/defective article judgment, the judgment including at least non-defective articles out of the non-defective articles, intermediate articles, and defective articles is referred to as non-objective judgment, whereas the judgment including at least the defective articles is referred to as defective judgment.

Also in the foregoing description, the "evaluations at the image processing units" may take the form of a grade evaluation. In the case of a five-grade evaluation, for example, an article with high possibility of being non-defective is evaluated or rated at grade 5, an article with slight possibility of being non-defective is rated at grade 4, an article tending to be non-defective is rated at grade 3, an article with slight possibility of being defective is rated at grade 2, and an article with high possibility of being defective is rated at grade 1.

When the image processing device 3 judges the article to be intermediate or defective, the corresponding judgment is notified to the human operator. This may be done by indicating the occurrence of an intermediate article or a defective article on the monitor 40 together with an image of the intermediate or defective article. On the other hand, when the judgment shows a non-defective article, this means that there is no underlying problem to further continue the extruding operation and, accordingly, no notification is given to the human operator.

When the aluminum extruded shape is judged to be defective, the operator stops the extruding machine 4 to interrupt the extruding operation for taking an appropriate preventive measure against the external defect. When the external defect prevention measure has completed, the extruding machine 4 is started again to resume the extruding operation.

In the case where the aluminum extruded shape is judged to be an intermediate article, the same aluminum extruded shape is then subjected to a visual inspection performed by the human operator and if it is judged to be an defective article, the same operation as described at the preceding paragraph will be performed.

The image processing device 3 and the control unit (not shown) of the extruding machine 4 are electrically connected with each other so that when the image processing device 3 has passed a judgment of the defective or intermediate article, it issues a signal to the control unit to stop operation of the extruding machine 4 or perform control of the extrusion speed automatically. With this arrangement, the number of defective articles can be reduced.

It is possible according to the invention to arrange the monitor 10 such that it also displays an article, which has been judged to be non-defective.

The foregoing inspection of the external defects of the aluminum extruded shape may be performed after the aluminum extruded shape is subjected to a surface treatment, such as alumite treatment or painting process, effected after extrusion.

In this instance, in order to accomplish the foregoing defects inspection, the image processing device 4 is provided with the weighting unit 20, as shown in FIG. 1, which gives weights (or degrees of importance) to the respective judgments by the first to fifth evaluation parts $9_5$ to $9_5$, in accordance with the surface treatment effected on the aluminum extruded shape.

For instance, according to the thickness of an alumite film or the color of a paint, such as gold or white, the magnitude of respective judging reference values in the first to fifth evaluation parts $9_5$ to $9_5$ is set such that the quality of surface conditions, which may vary with the degree of external defect leading to a judgment of the defective article, can be changed according to the surface treatment.

Furthermore, the visual inspection apparatus of the present invention may be installed at both a first position immediately downstream of an extruding station and a second position downstream of a post-extrusion treatment station where a surface treatment such as alumite treatment or coating is performed. In this instance, it is checked whether an aluminum extruded shape, which has already been judged to be non-defective by the inspection at the first position, is judged to be defective by the inspection at the second position. When judged to be non-defective, the judgment is affirmed. Alternatively, when judged to be defective, the weighting process may be modified to prevent the external defect from recurring.

INDUSTRIAL APPLICABILITY

As described above, according to the present invention, evaluations obtained by the respective image processing units with respect to set judging reference values are weighted to check whether surface conditions are so inferior as to render the article unusable as a product. This arrangement provides advantageous effects that non-defective articles and defective articles can be surely distinguished and, unlike the visual observation, the judgment can be done under certain standard. Furthermore, particularly when this arrangement is applied to an aluminum extruded shape, the quality of surface conditions based on external defects, such as streaks, dice marks and rough surfaces occurring on the surface thereof can be detected reliably.

The invention claimed is:

1. An article visual inspection apparatus comprising:
   an imaging device (1) for imaging a surface of an article; and
   an image processing device (3) that captures an image picked up by the imaging device (1),
   wherein the image processing device (3) has a plurality of image processing units ($10_1$, $10_2$, $10_3$, $10_4$, $10_5$),
   each of the image processing units compares a captured image with a judging reference value set for each image processing unit to evaluate the result,
   the image processing device (3) further includes a weighting unit (20), and
   the weighting unit performs a weighting of evaluations of the respective image processing units to thereby judge whether to accept or reject the article.

2. The article visual inspection apparatus according to claim 1, wherein the plurality of image processing units ($10_1$, $10_2$, $10_3$, $10_4$, $10_5$) is configured to perform the functions of:
   detecting a brightness of the captured image within a set inspection area (a), and comparing the detected brightness with a judgment reference value to evaluate the result;

dividing the inspection area of the captured image into a plurality of inspection blocks (a-1, a-2, a-3), detecting a brightness of the captured image in each of the inspection blocks, and comparing the detected brightness with a judging reference value to evaluate the result; and setting a small region (Y) within the inspection area of the captured image, moving the small region, detecting a brightness of the captured image in the small region while the small region is present at each of a plurality of preset position during movement, and comparing the detected brightness with a judging reference value to evaluate the result.

3. The article visual inspection apparatus according to claim 1, wherein the image processing device (3) includes a first image processing unit ($10_1$), a second image processing unit ($10_2$), a third image processing unit ($10_3$), a fourth image processing unit ($10_4$) and a fifth image processing unit ($10_5$), wherein the first image processing unit ($10_1$) compares a brightness difference between a light part and a dark part of the captured image with a first judging reference value to evaluate the result, the second image processing unit ($10_2$) compares a brightness difference rate of the dark part to the light part with a second judging reference value to evaluate the result, the third image processing unit ($10_3$) divides the captured image into a plurality of inspection blocks (a-1, a-2, a-3), calculate a brightness difference in each of the divided inspection blocks, and compares the number of inspection blocks having brightness differences greater than a brightness difference threshold value with a third judging reference value to evaluate the result, the fourth image processing unit ($10_4$) divides the captured image into a plurality of inspection blocks (a-1, a-2, a-3), calculates a maximum average brightness difference on the basis of an average brightness in each of the divided inspection blocks, and compares the maximum average brightness difference with a fourth judging reference value to evaluate the result, and the fifth image processing unit ($10_5$) calculates a brightness kurtosis in each of plural small regions of the captured image, and compares a maximum brightness kurtosis of the calculated brightness kurtosis values with a fifth judging reference value to evaluate the result.

4. The article visual inspection apparatus according to claim 1, wherein the weighting unit (20) multiplies evaluations detected by the respective image processing units by weighting factors, respectively, adds up all the multiplied values, and compares the sum with a judging reference value to judge whether to accept or reject the article.

5. The article visual inspection apparatus according to claim 1, wherein the article to be imaged is an aluminum extruded shape (5), and wherein the imaging device (1) is disposed on an extrusion side of an extruding machine (4) for imaging a surface of the aluminum extruded shape immediately after extrusion thereof, the image processing device (3) further includes a preprocessing unit (7) for preprocessing the captured image, and the preprocessing unit (7) has a function to correct an image blurring occurring due to vibrations of the aluminum extruded shape during extrusion to thereby form an image free of blurring.

* * * * *